United States Patent
Hallerman et al.

[19]

[11] Patent Number: 6,144,453
[45] Date of Patent: Nov. 7, 2000

[54] SYSTEM AND METHOD FOR THREE-DIMENSIONAL INSPECTION USING PATTERNED LIGHT PROJECTION

[75] Inventors: Gregory R. Hallerman, Hollis, N.H.; Jonathan E. Ludlow, Lexington, Mass.; Howard K. Stern, Green Lawn, N.Y.

[73] Assignee: Acuity Imaging, LLC, Nashua, N.H.

[21] Appl. No.: 09/412,349

[22] Filed: Oct. 5, 1999

Related U.S. Application Data

[62] Division of application No. 09/150,716, Sep. 10, 1998.

[51] Int. Cl.⁷ ................................................. G01B 11/25
[52] U.S. Cl. ............................................................. 356/376
[58] Field of Search ........................................... 356/376

[56] References Cited

U.S. PATENT DOCUMENTS

| | | | |
|---|---|---|---|
| 4,175,862 | 11/1979 | DiMatteo et al. | 356/375 |
| 4,269,513 | 5/1981 | DiMatteo et al. | 356/376 |
| 4,508,452 | 4/1985 | DiMatteo et al. | 356/375 |
| 4,511,252 | 4/1985 | DiMatteo et al. | 356/375 |
| 4,682,894 | 7/1987 | Schmidt et al. | 356/375 |
| 4,981,360 | 1/1991 | Schwartz | 356/376 |
| 4,984,893 | 1/1991 | Lange | 356/376 |
| 5,097,516 | 3/1992 | Amir | 382/1 |
| 5,175,601 | 12/1992 | Fitts | 356/376 |
| 5,646,733 | 7/1997 | Bieman | 356/376 |
| 5,999,266 | 12/1999 | Takahashi et al. | 356/376 |

OTHER PUBLICATIONS

Windecker et al "Topometry of technical and biological objects by fringe projection." *Applied Optics*, vol. 34, No. 19, (Jul. 1, 1995) pp. 3644–3649.

ICOS, BGA 3D Inspection System, Nov. 1996.

Windecker & Tiziani, Topometry of technical and biological objects by fringe projection, Jul. 1995, pp. 3644–3650, Applied Optics vol. 34, No. 19.

*Primary Examiner*—Richard A. Rosenberger
*Attorney, Agent, or Firm*—Borque & Associates, P.A.

[57] ABSTRACT

A three-dimensional inspection system is used to obtain three-dimensional information pertaining to an article having specular surfaces, such as a BGA device, by projecting a pattern of light onto the article at an oblique angle with respect to the article. The system includes patterned light projector having an optical axis disposed at an oblique angle with respect to the plane of the article being inspected and an image detector or camera disposed generally above the article being inspected to detect the image of the pattern projected on the article. The patterned light projector includes an extended light source that directs light along the optical axis and a light patterning member disposed at an angle with respect to the optical axis such that the light pattern is in focus in an image plane parallel to the plane of the article, thereby satisfying the Scheimpflug condition. The light pattern preferably includes lines of light projected onto the article with a substantially equal thickness and spacing. The spacing of the lines is preferably greater than a spacing or pitch of the specular elements, such as the solder balls on a BGA device. An image processor is coupled to the image detector to receive the image, locate the lines, and measure the lateral shift of the lines. Height information is determined from the lateral shift and projection angle using triangulation.

7 Claims, 11 Drawing Sheets

SYSTEM AND METHOD FOR THREE-DIMENSIONAL INSPECTION USING PATTERNED LIGHT PROJECTION

This application is a divisional of U.S. patent application Ser. No. 09/150,716 filed Sep. 10, 1998.

STATEMENT OF GOVERNMENT SUPPORT

This invention was made with Government support under Contract No. DAAH01-96-CR208 awarded by the Department of the Army. The government has certain rights in the invention.

FIELD OF THE INVENTION

The present invention relates to systems and methods for three-dimensional inspection of articles and more particularly, to a system and method for three-dimensional inspection of electronic packages, such as ball grid array (BGA) devices, using a projected pattern of light.

BACKGROUND OF THE INVENTION

Figure 1:
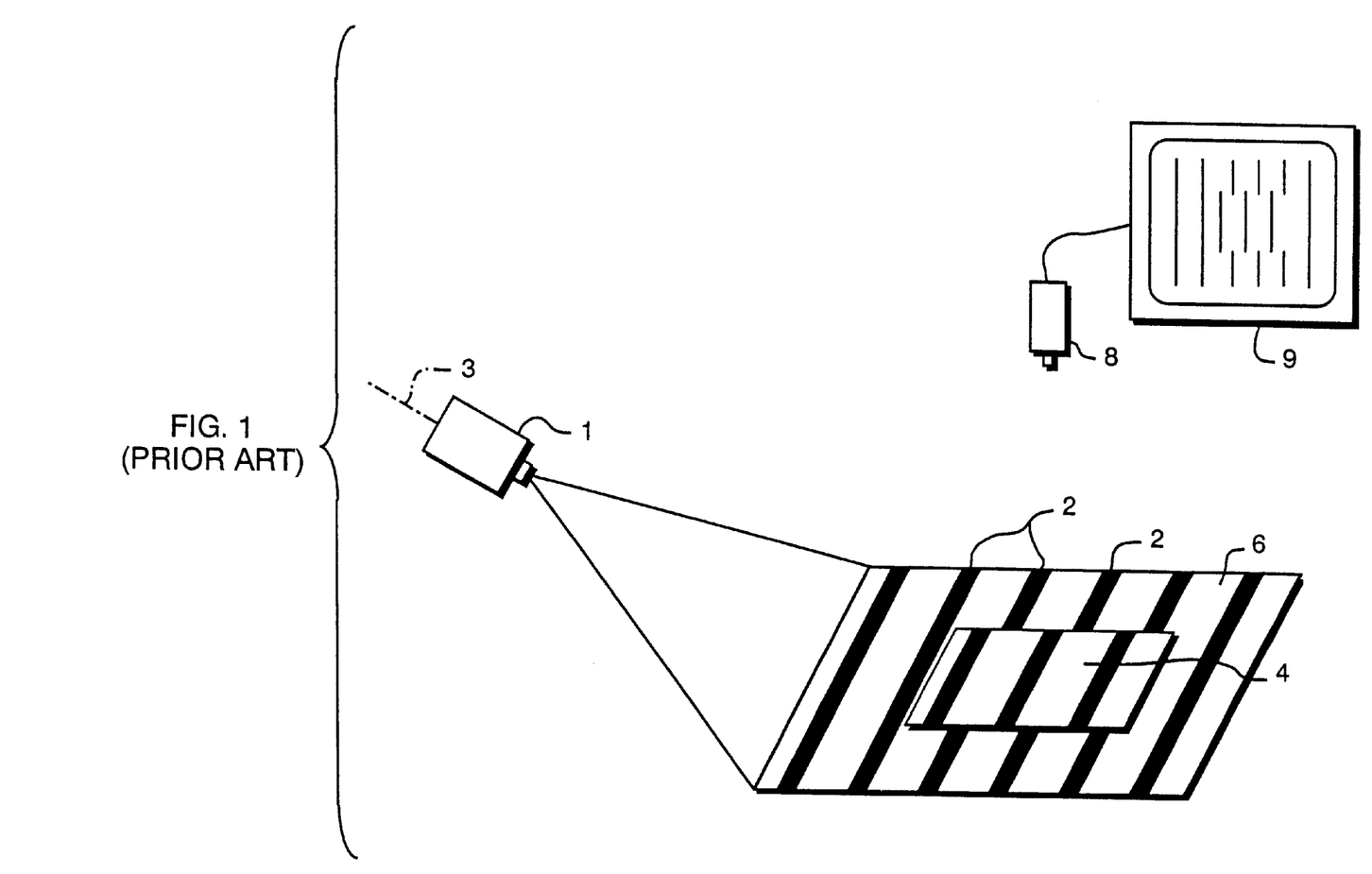
FIG. 1 is a schematic view of a prior art system for using a projected pattern of lines to determine three-dimensional features.

Projecting patterned or structured light onto an article is a well known technique for obtaining three-dimensional information pertaining to the article. As shown in FIG. 1, a projector 1 is used to project a pattern of light, such as a series of parallel lines 2, onto surfaces 4, 6. The axis 3 of the projector 1 is oriented at an angle with respect to these surfaces 4, 6. When the lines 2 are projected onto a surface 4 that is raised with respect to another surface 6, the lines 2 appear to shift laterally between these surfaces 4, 6 when viewed from above, for example, using camera 8 and monitor 9. The magnitude of the lateral shift between the lines 2 on surfaces 4, 6 yields information about the distance between the surface 4 and the surface 6. For example, the lateral shift between the lines 2 and the angle of projection can be used to calculate the height of the surface 4 with respect to the surface 6 using triangulation.

Existing systems and methods for three-dimensional inspection using projected light patterns, however, do not adequately provide an accurate inspection of electronic packages having specular surfaces, such as Ball Grid Array (BGA) devices. Accurate inspection of electronic packages and other such articles requires high resolution measurements of the lateral shift in the lines or pattern projected onto the article. If the projected pattern or image is not properly focused or is distorted, measurements of the lateral shift in the lines of the projected pattern may not be accurate. In the existing systems having an angled projector 1, the projected image may not be in focus if the Scheimpflug condition is not satisfied, as will be discussed in greater detail below. Blurring of the lines in the projected pattern also typically occurs as the lines move away from the focus of the projector 1. As a result, the width of the lines projected onto the article may not be consistent over the entire range of the article being inspected. The width and spacing of the projected lines can also vary as a result of an effect commonly referred to as keystoning, as will be described in greater detail below.

Existing patterned light projectors also encounter problems as a result of specular surfaces, such as the solder balls on BGA devices. The reflection of light from specular surfaces often causes a saturation of pixels in the camera and necessitates the use of cameras with high dynamic ranges or logarithmic responses. Also, if a series of lines or a similar pattern is projected with a spacing equal to the spacing of the solder balls on a BGA device, light will reflect between neighboring solder balls. This type of reflection will adversely affect the image detected by the camera and thus will result in an inaccurate measurement of the shift in the lines. Furthermore, when the article being inspected has a surface and surface objects with different reflectivities, such as the solder balls and the substrate of a BGA device, it is difficult to view both surfaces with a single exposure without losing information on one of the surfaces by either saturating one of the lines or causing one to be in the noise.

Accordingly, a need exists for a system and method for three-dimensional inspection that projects patterned light in a manner that reduces unwanted reflection from specular surfaces, provides a projected pattern that is in focus, and allows high resolution measurements of the reflected light pattern to accurately determine three-dimensional information. In particular, a need exists for a system and method for three-dimensional inspection of BGA devices or similar articles having rounded specular surfaces and surfaces of different reflectivities.

SUMMARY OF THE INVENTION

The present invention features a system for three-dimensional inspection of an article having at least one three-dimensional object protruding from or on the surface of an article to be inspected and which article is supported generally in a plane. A patterned light projector having an optical axis is disposed at an oblique angle with respect to the plane of the article. The patterned light projector includes a light source for generating light and directing the light toward the article along the optical axis. A light patterning member is disposed between the light source and the article at an oblique angle with respect to the optical axis, for creating the light pattern as the light passes through the light patterning member.

The system also comprises a light pattern detector, for detecting the light pattern reflected from the surface of the article. In one example, the light pattern detector includes an image detector, such as a camera, disposed generally above the article, for detecting the image of the light pattern reflecting from the article. The image of the light pattern is preferably in a plane parallel to the plane of the article such that the light pattern projected onto the article and the article itself are simultaneously in focus. The system also comprises an image processor, for receiving the image detected by the image detector and for processing the image to determine three-dimensional information pertaining to the article.

The present invention also features a patterned light projector for use in the system for three-dimensional inspection of an article. The preferred embodiment of the patterned light projector includes an extended light source for generating light and projecting the light toward the article generally along the optical axis disposed at an oblique angle with respect to the plane of the article. The light patterning member preferably includes a pattern of lines and creates lines of light projected onto the article.

The patterned light projector also includes one or more projection lenses disposed between the light patterning device and the article, for projecting the light pattern on the surface of the article. A condenser lens is also preferably disposed between the extended light source and the light patterning member, for providing a substantially uniform illumination of the light patterning member.

Examples of the extended light source include a fiber optic bundle, a light line, or an array of light emitting diodes (LEDs). In one example, the light patterning member includes a transparent slide with a mask forming the pattern of lines. Alternatively, the light patterning member includes a programmable mask.

The pattern of lines on the light patterning member preferably have a varying, non-uniform spacing and thickness such that the lines of light projected onto the article at the oblique angle have a substantially equal spacing and thickness on and along the surface of the article. The spacing of the lines of light is preferably greater than the spacing of the specular elements or objects on the article being inspected, for example, the solder balls on the BGA device.

The patterned light projector also preferably includes a depth of focus modifier, for providing a lower f-number (i.e. less depth of focus) in a direction along a length of the lines of light projected on the surface of the article, and a higher f-number (i.e. greater depth of focus) in a direction along a width of the lines. This provides very crisp, clear edges on the projected lines. In one example, first and second projection lenses are used with an elongated aperture disposed between the first and second projection lenses and oriented lengthwise with respect to the lines.

According to one embodiment, the projector shifts the lines of light projected onto the article. The shifting can be accomplished by a mechanism for moving the projector, a rotatable transparent light shifting plate disposed between the patterned light projector and the article, or a programmable mask.

The present invention also features a method of inspecting three-dimensional features of an article having an array of rounded specular elements. The method comprises the steps of: placing the article on an article support such that the article generally lies in a plane; projecting lines of light onto the article, wherein a spacing of the lines of light is greater than a spacing of the rounded specular elements such that one of the lines of light approaches a top of one of the rounded specular elements while a consecutive one of the lines is on an opposite side of a consecutive one of the rounded specular elements; detecting at least a first image of the lines of light projected on to the article at a first position; and processing the first image to locate at least one of the lines of light projected on the planar surface of the article and to measure a lateral shift of the one line of light at a point on one of the rounded specular elements, for calculating a height of the rounded specular element at that point. In one example, the article includes a BGA device having an array of solder balls disposed on a substrate such that the spacing of the lines is greater than a pitch of the array of solder balls.

The preferred method further includes shifting the lines of light projected onto the article by a fraction of a projected line width to a second position and detecting a second image of the lines of light at the second position. The step of locating the lines includes subtracting gray scale values in the second image of the line from corresponding (i.e., same pixel) gray scale values in the first image of the line to obtain a synthetic image of the line. The synthetic image extends through a zero crossing plane and includes positive pixel values above the zero crossing plane and negative pixel values below the zero crossing plane. The points at which the synthetic image intersects the zero crossing plane are located and used to calculate the lateral shift of the line.

The step of locating the points at which the synthetic image intersect the zero crossing plane includes fitting a surface using a plurality of best fit splines to a portion of the synthetic image proximate said zero crossing plane and determining where the best fit splines intersect the zero crossing plane. Alternatively, a local best fit plane can be fit to a small portion of the synthetic image proximate the zero crossing plane.

DESCRIPTION OF THE DRAWINGS

These and other features and advantages of the present invention will be better understood by reading the following detailed description, taken together with the drawings wherein.

DETAILED DESCRIPTION OF THE PREFERRED EMBODIMENT

Figure 2:
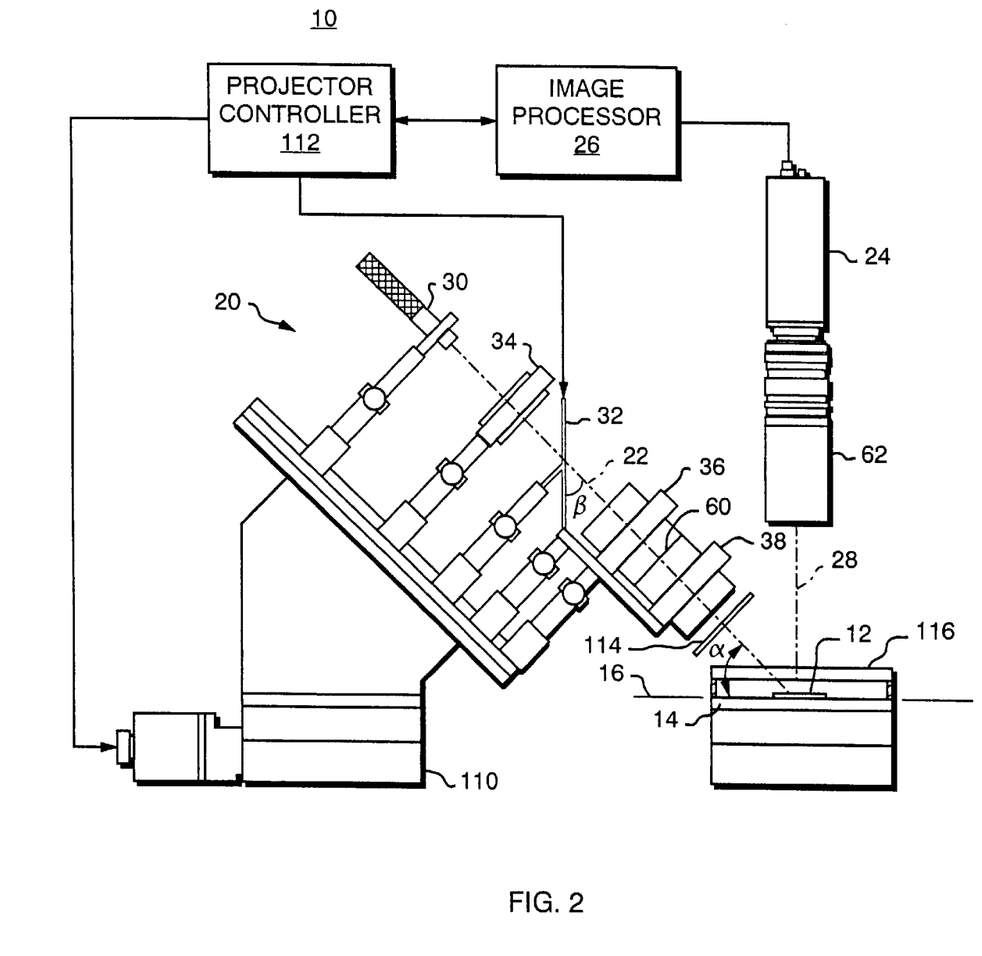
FIG. 2 is a schematic side view of a three-dimensional inspection system using a projected light pattern, according to the present invention.

The three-dimensional inspection system 10, FIG. 2, according to the present invention, projects a light pattern, such as a pattern of lines, onto the surface of an article 12 to be inspected, such as a BGA device, and analyzes the reflected light pattern to determine three-dimensional characteristics of the surface of the article 12. In general, the three-dimensional inspection system 10 includes an article support 14 that supports the article 12 generally in a plane 16, and a patterned light projector 20 that projects the pattern of light generally along an optical axis 22 onto the article 12 with the optical axis 22 of the projector 20 at an oblique angle a with respect to the plane 16 of the article 12. A light pattern (or image) detector 24, such as a CCD camera, detects the light pattern (or image) projected onto the article 12, and a light pattern (or image) processor 26 receives the reflected light pattern or image detected by the image detector 24 and processes the image to determine three-dimensional information pertaining to the article 12.

The patterned light projector 20 includes a light source 30 that generates light and projects the light generally in the direction of the optical axis 22. A light patterning member 32 is disposed between the light source 30 and article 12, for creating the light pattern as the light passes through the light patterning member 32. A condenser lens 34 is optionally disposed between the light source 30 and light patterning member 32. The light source 30 and condenser lens 34 (when used) provide a substantially uniform illumination of the light patterning member 32. The patterned light projector 20 also includes one or more projection lenses 36, 38 that project the pattern of light onto the article 12 generally along the optical axis 22. In one example, the projection lenses 36, 38 include two 100 mm Cook triplets (such as Part No. 01LAS007 available from Melles Griot) used in a symmetrical relationship back-to-back.

The light source 30 used in the patterned light projector 20 is preferably an extended light source, such as a large fiber optic bundle, a light line, or an array of light emitting diodes (LEDs). By using an extended light source, the light propagates from a sizable area rather than a single point (i.e., when using a point source). Since the light projected onto the article 12 comes from a wide range of angles, not just a single angle, this type of illumination is advantageous for articles 12 having surfaces that are specular in nature (e.g., solder balls) disposed on surfaces having a low reflectivity (e.g., the substrate of BGA devices). The light reflected from the specular surfaces on the article 12 is thus more diffuse in nature as a result of the extended light source and reduces saturation in the image detector or camera 24. When saturation is reduced, the need for cameras with high dynamic ranges or logarithmic responses is eliminated. Although the exemplary embodiment in FIG. 2 shows a fiber optic type light source 30 used with the condenser lens 34, other types of illumination can be used and the condenser lens 34 is not needed for all types of illumination.

Figure 3:
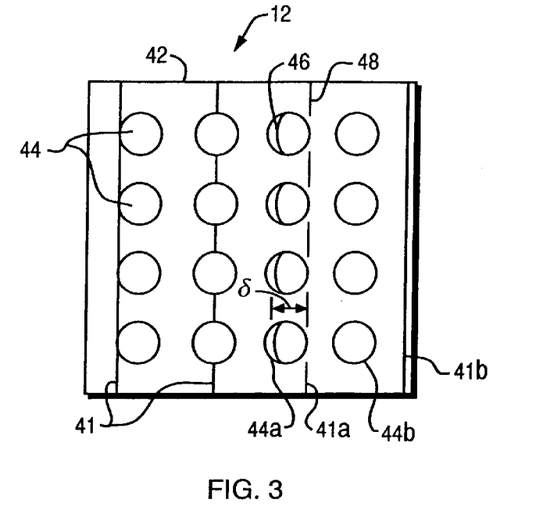
FIG. 3 is plan view of a BGA device having a pattern of lines of light projected thereon, according to one embodiment of the present invention.

According to the exemplary embodiment, the light pattern is a pattern of generally straight, parallel lines 41, FIG. 3, projected onto the article 12, although the present invention contemplates other projected patterns of light. The light passing through the light patterning member 32 creates light planes 40, FIGS. 4, that form the image of parallel lines 41 when projected onto the article 12. In one embodiment, the light patterning member 32 is a transparent slide, such as glass, with a mask formed on the transparent slide to create the light planes 40 as the light passes through. Alternatively, the light patterning member 32 may include a programmable mask, such as a liquid crystal display (LCD).

One example of the article 12 to be inspected includes a substrate 42 having an array of rounded specular elements 44, such as an array of solder balls on a BGA device. As each line image 41 passes over the rounded specular elements 44 on the article 12, the line image 41 appears to shift laterally when viewed from above (FIG. 3). Thus, the image of a reflected line 41a passing over rounded specular elements 44 includes a portion 46 reflected from the higher surface of the rounded specular elements 44 and a portion 48 reflected from the generally lower planar surface of the substrate 42. On the rounded specular elements 44, the lateral shift δ of each line portion 46 varies as the height h of the rounded element 44 varies. Although the exemplary embodiment shows a BGA device, the present invention also contemplates using the three-dimensional inspection system to inspect other types of electronic packages or other articles having three-dimensional surfaces.

Figure 4:
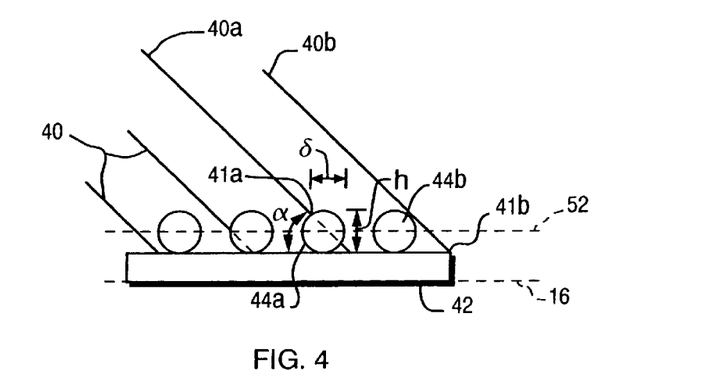
FIG. 4 is a side view of a BGA device having a pattern of lines of light projected thereon, according to one embodiment of the present invention.

According to the preferred exemplary embodiment, the lines 41 have a spacing that is greater than the spacing of the rounded specular elements 44, i.e., the pitch of the BGA device. The lines 41 are spaced such that when one of the line images 41a approaches the top of an element 44a, the next subsequent line 41b is on the opposite side of the next subsequent element 44b (FIGS. 3 and 4). For example, if a BGA device has a pitch of 0.050" and the solder balls have a diameter of 0.030", a preferred line spacing is roughly 0.075". By providing a spacing of the line images 41 that is greater than the spacing or pitch of the solder balls or other specular elements 44, the amount of reflections between the balls or specular elements is reduced, preventing the degradation of line position measurements.

Figure 5:
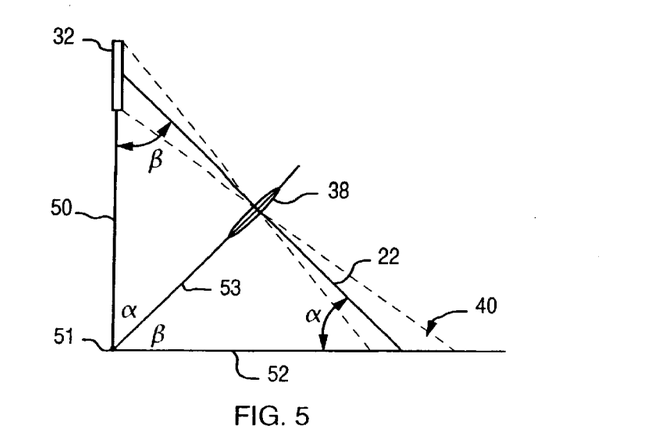
FIG. 5 is a side schematic view of an arrangement of the light patterning member in the patterned light projector to satisfy the Scheimpflug condition, according to the present invention.

According to the preferred embodiment, the projector 20 projects the lines such that the image of the lines is preferably in focus in a desired plane 52 parallel to the plane 16 of the article. For inspection of BGA and other similar devices, the desired plane 52 is parallel to the substrate 42 and lies about half-way between the substrate 42 and the tops of the rounded specular elements (solder balls) 44. To focus the line images 41 in this desired plane 52, the light patterning member 32, FIG. 5, is preferably oriented at an oblique angle β with respect to the optical axis 22. Since the article 12 (FIG. 2) lies in the plane 16 having an angle a with respect to the optical axis 22, the light patterning member 32 should also be angled with respect to the optical axis 22 to satisfy the Scheimpflug condition. The Scheimpflug condition is satisfied when the plane 50 of the object or light patterning member 32, the plane 52 of the line image, and the plane 53 of the lens 38 all intersect at a common line 51. Thus, the light patterning member 32 is angled at the angle β with respect to the optical axis 22 and is positioned relative to the lens 38 such that the desired image plane 52 is parallel to plane 16 of the article 12. The angles α and β are preferably both about 45°.

Figure 6:
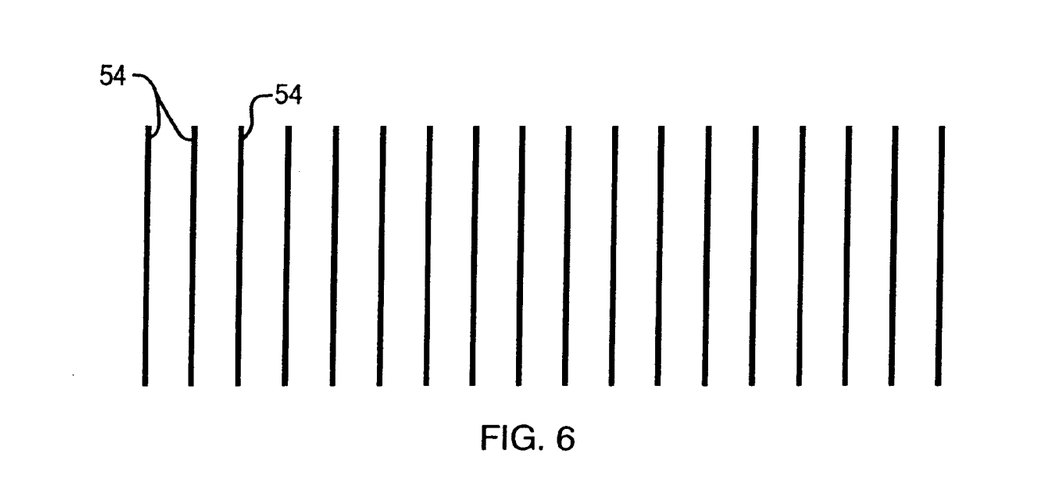
FIG. 6 is a schematic representation of a pattern of lines having a substantially equal spacing and thickness.
Figure 7:
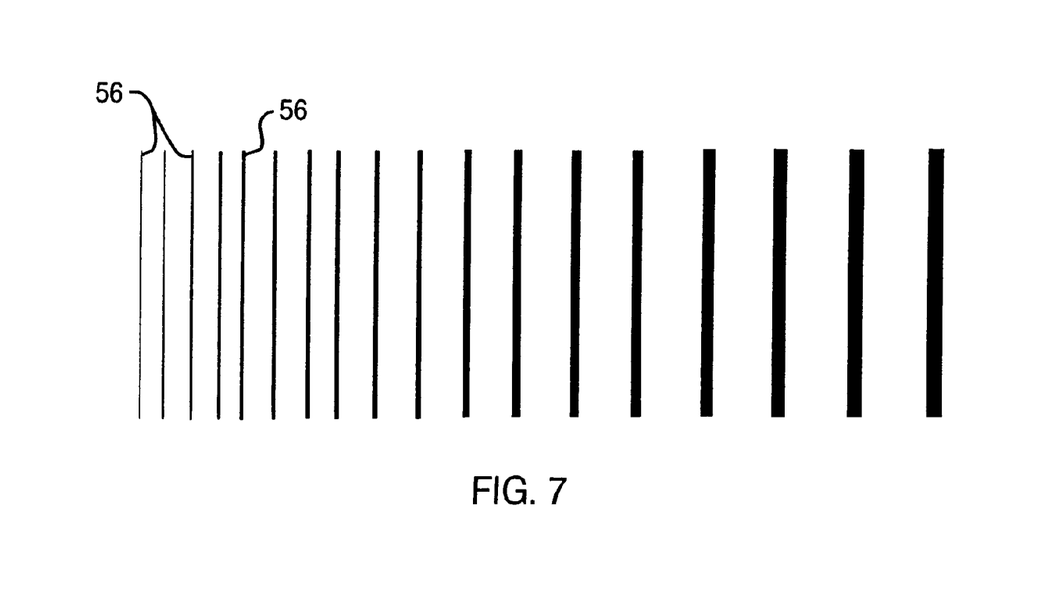
FIG. 7 is a schematic representation of a pattern of lines having a varying spacing and thickness to prevent keystoning, according to one embodiment of the present invention.

As a result of angling the light patterning member 32 with respect to the optical axis 22, the pattern on the light patterning member 32 will be distorted as the pattern is projected onto the article 12—an effect commonly referred to as keystoning. For example, if a light patterning member 32 has a pattern of equally spaced, equal thickness lines 54, FIG. 6, the light planes passing through the light patterning member at the angle β will create lines 54, FIG. 7, having a varying spacing and thickness. Thus, the light patterning member 32 is preferably an anti-keystoning slide having a pattern of lines with a varying spacing and thickness to produce a projected pattern of lines on the article 12 having a substantially equal spacing and equal thickness. An anti-keystoning slide produces the opposite effect in that a pattern of lines having a varying spacing and thickness (as shown in FIG. 7) is provided on the light patterning member or slide 32 to yield a projected pattern of substantially equally spaced, equal thickness lines (as shown in FIG. 6).

One way of creating a light patterning member 32 having a pattern of lines that provide anti-keystoning is to place an illuminated pattern of evenly spaced equal thickness lines in the workspace on the article support 14 (FIG. 2). A film plate is placed in the position of the light patterning member 32 and is exposed to the illuminated pattern of evenly spaced equal thickness lines on the article support 14 through the projection lens system 36, 38. Since the light rays through the system are reversible, the developed plate will have a pattern of lines with the varying spacing and thickness needed to correct the keystoning effect. Alternatively, the process can be simulated on a computer and the computer output can be used to print, expose, cut or otherwise generate a light patterning member or mask having the desired anti-keystoning pattern.

According to the preferred embodiment, the patterned light projector 20 (FIG. 2) also provides a depth of focus modifier 60 that provides different f-numbers in the horizontal and vertical directions. The depth of focus modifier 60 is preferably an elongated aperture 61, FIG. 8, such as a narrow rectangular slit, disposed between the projection lenses 36, 38 such that the aperture 61 is oriented in the same direction as the lines in the projected light pattern. The aperture 61 provides a lower f-number in the direction of arrows 64 along the length of the aperture 61 (also along the length of the projected lines) and a higher f-number in the direction of arrows 66 along the width of the aperture 61 (also along the width of the projected lines).

For example, if the lines on the light patterning member 32 are disposed vertically, the elongated aperture 61 disposed between the lenses 36, 38 is oriented vertically to yield a higher f-number in the horizontal direction of the lines than in the vertical direction. In one example, the aperture 61 has a width in a range of about 1 mm and a length in a range of about 50 mm resulting in a greater depth of focus in one direction by a factor of 50.

Figure 8:
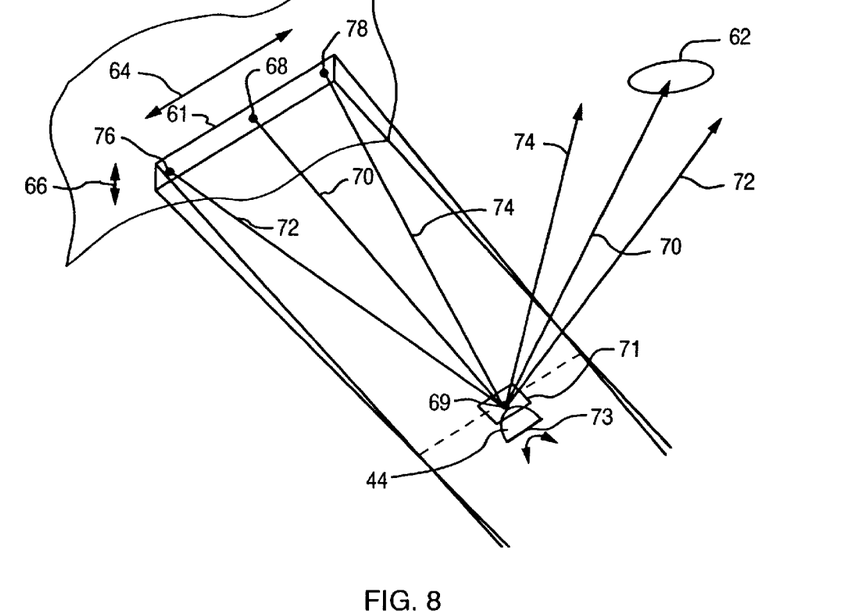
FIG. 8 is a schematic view of the elongated aperture used in the patterned light projector to modify the depth of focus, according to the present invention.

The low f-number in the direction 64 along the length of the lines is important for the purpose of illuminating each point on the rounded specular objects from a wide angular distribution. This reduces the dynamic range needed by the image detector or camera 24 that gathers the reflected energy from the rounded specular objects. The aperture 61 does this by reducing the "hot spot" energy reflected by a directly reflecting specular point as compared to the energy reflected by a diffusely reflecting point. The directly reflecting specular point sends energy from only one small portion 68 of the elongated aperture 61 into a lens 62 of the image detector or camera 24. A diffuse point absorbs energy from the entire elongated aperture 61 and reflects a portion of that energy into the camera lens 62.

The elongated aperture 61 also ensures that a greater variety of specular points on the rounded specular elements 44 (e.g., solder balls) become directly reflecting and visible to the camera lens 62. The light ray 70 from the portion 68 at the center of the elongated aperture 61 is directed from a specularly reflecting point 69 on a rounded specular element 44 into the lens 62. Other points on the rounded specular element 44 direct light rays 72, 74 from portions 76, 78 at the outer extent of the elongated aperture 61 into the lens 62. As an analogy, a specular point 69 on a curved or rounded surface or element 44 can be approximated by a tiny flat mirror 71 tangent to the curved or rounded surface 44 at that specular point 69. An image of the camera lens 62 is present in the tiny flat mirror 71. Any light rays (e.g., light ray 70 from the center point 68 of the aperture 61) that pass through both the specular point 69 and the image of the camera lens 62 in the tiny flat mirror 71 will be specularly reflected into the camera lens 62. Any light rays (e.g., light rays 72, 74 from the outer points 76, 78 of the aperture 61) that do not pass through the specular point 69 and the image of the camera lens 62 in the mirror 71 will be specularly reflected away from the camera lens 62. Other specular points on the curved or rounded surface 44 can be approximated by rotating the mirror 71 about an axis 73, which has the effect of directing the light rays 72, 74 from the outer points 76, 78 of the aperture 61 into the camera lens 62.

Figure 9:
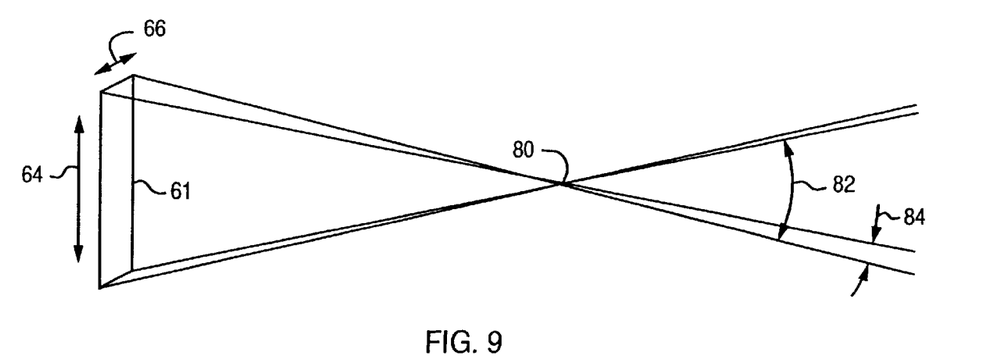
FIG. 9 is a schematic representation of the elongated aperture providing a short depth of focus along the length of the projected lines and a long depth of focus along the width of the projected lines, according to the present invention.

The low f-number of the elongated aperture 61, FIG. 9, along the length direction 64 provides a rapid divergence and a short depth of focus from the focused spot 80, as indicated by arrows 82. The high f-number along the width direction 66 provides slow divergence and a long depth of focus from the focused spot 80, as indicated by arrows 84. The high divergence and resulting short depth of focus cannot be discerned in the direction along the length of the lines, since there is no detail to show a de-focus in that direction. Thus, as the lines move away from the focus of the projector 20, the lines will blur more rapidly in length than in width, thereby maintaining a substantially constant line width over the entire range of the article 12. A substantially constant line width over the entire range of the article 12 allows higher resolution measurements. Accordingly, using an elongated aperture, such as a rectangular slit, in lieu of a more commonly used circular aperture allows for a greater depth of focus while also allowing sufficient light to reach the article 12.

The elongated aperture 61 is preferably placed at the common focal point of the two projection lenses 36, 38, thereby making the overall projection lens system telecentric in one axis only. This provides constant magnification in the direction transverse to the projected lines, which has the effect of keeping the spacing between the projected lines constant, i.e., neither converging nor diverging, regardless of the longitudinal distance from the lenses 36, 38 along the projection axis 22.

A method of inspecting three-dimensional features of an article 12 according to the present invention begins by placing the article 12, such as a BGA device, on the article support 14 beneath the image detector or camera 24 (See FIG. 2). The camera 24 is preferably disposed above the article 12 with an axis 28 of the camera 24 generally perpendicular to the plane 16 of the article 12. Alternatively, the camera 24 can also be disposed at an acute angle with respect to the plane 16 of the article 12. The light planes 40 are then projected onto the article 12 at the oblique angle α with respect to the plane 16 of the article 12 to form the image of the lines 41 (FIGS. 3 and 4).

The image of the lines 41 reflected from the article 12 are then detected by the image detector or camera 24. In one example, the lens 62 of the image detector 24 includes a telecentric gauging lens. A telecentric gauging lens keeps the object constant as the camera 24 goes in and out of focus. The whole field is viewed from the same perspective angle, in contrast to a standard lens where the closer the object is, the greater the magnification. The image detector 24 can be calibrated, for example, using the method of calibrating a three-dimensional sensor disclosed in U.S. Pat. No. 4,682,894, incorporated herein by reference.

The detected image is received by the image processor 26, which locates the line images 41 projected onto the article 12, as described in detail below, and measures the lateral shift δ along each of the line images 41 (FIG. 3). Using the lateral shift δ at any given point on the specular element 44 and the projection angle α, the height h at that point on the element 44 can be calculated by triangulation.

Figure 10A:
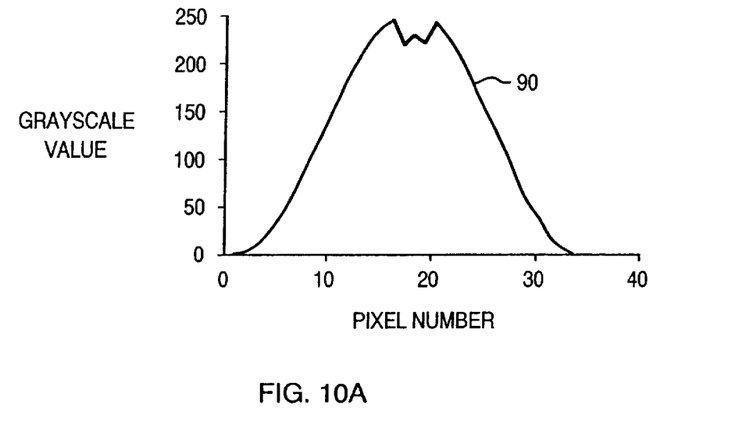
FIG. 10A is a diagrammatic view of a projected line image profile taken across the width of a projected line image.

Each detected line image includes a series of pixels having gray scale values, which can be represented along a width of the line as a line image profile 90, FIG. 10A. Because the line image profile 90 is an irregular gaussian profile, attempting to locate the center of the line by finding the maximum gray scale value or attempting to locate the gray scale values at the edge of the line is not adequate for high resolution measurements. Thus, the preferred method of the present invention uses a technique, sometimes referred to as "line splitting" or "plane splitting", to locate the lines with less ambiguity than if a single line image profile 90 is used.

Figure 10B:
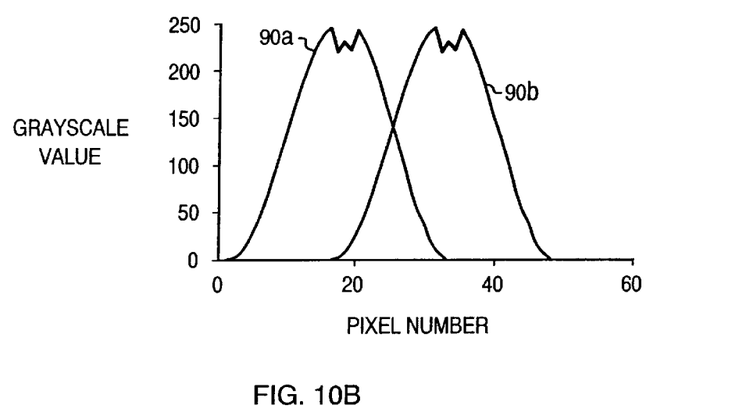
FIG. 10B is a diagrammatic view of projected line image profiles of a projected line image shifted from a first position to a second overlapping position, according to the method of the present invention.
Figure 10C:
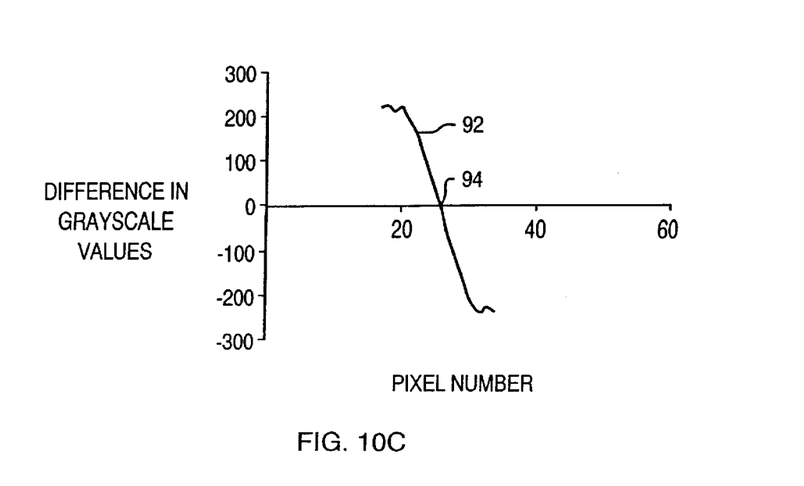
FIG. 10C is a diagrammatic view of a synthetic line image profile obtained by subtracting the projected line image at the second position from the projected line image at the first position, according to the method of the present invention.

According to this preferred method, each line is shifted by a fraction of a line width from a first position to a second overlapping position. First and second images of each line are taken at the first and second overlapping positions, as represented by first and second image profiles 90a, 90b, FIG. 10B. In one example, the line thickness is about 0.004" and the lines are shifted by about 0.002". The gray scale values of the second line image (represented by line image profile 90b) are subtracted from the corresponding (same pixel number) gray scale values of the first line image (represented by line image profile 90b) to obtain a computed or a synthetic line image, as represented by synthetic line image profile 92. The synthetic line image corresponds to the difference in gray scale values and has positive and negative gray scale values. The point 94 of zero amplitude between the resulting positive and negative peaks in the synthetic image corresponds to an imaginary light plane edge. The imaginary light plane edge is sharply defined because the edge slope at the zero crossing point 94 is twice the slope of the sides of the original light planes.

Figure 11:
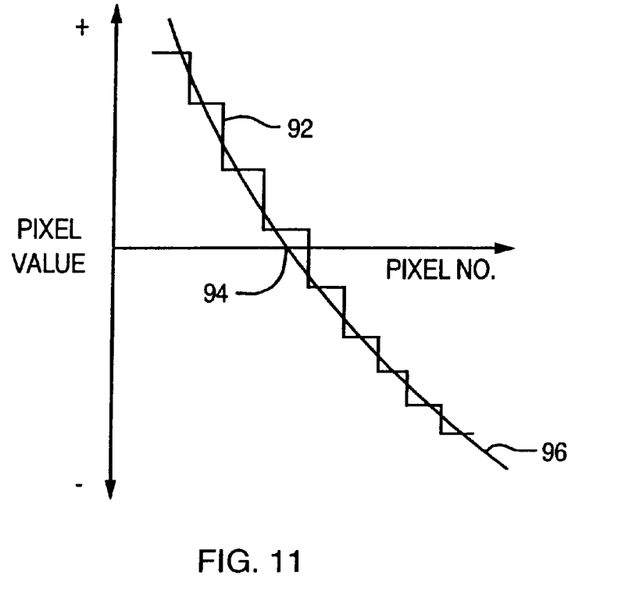
FIG. 11 is a diagrammatic view of a "best fit" spline fit to the synthetic line image profile, according to one method of the present invention.

The zero crossing point 94 of the synthetic line images is used to more accurately locate the line images and to measure the shift in the line images projected onto the article. According to the preferred method, a "best fit" spline 96, FIG. 11, is passed through the pixel values in the synthetic line image profile 92. The location where the spline 96 passes through the axis is computed to provide the best estimate of the location of the zero crossing point 94. This method of computing the location of the zero crossing point is preferred because pixel locations and pixel values are restricted to integers and noise is often present in images.

Figure 12:
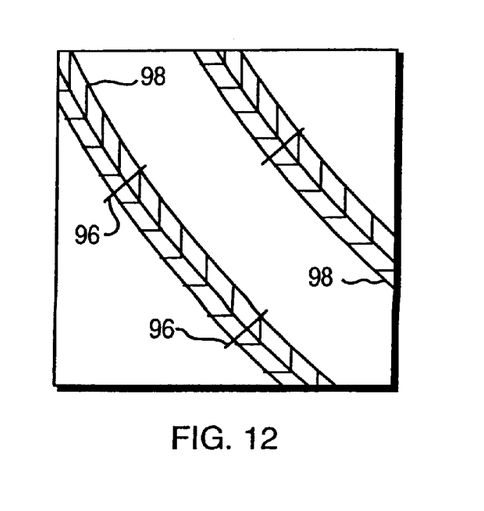
FIG. 12 is a top schematic view of synthetic line images obtained by subtracting the projected line images taken at the first and second overlapping positions, according to the method of the present invention.

Synthetic line images 98, FIG. 12, are computed for each of the detected line images. The direction of the cross-hatching in FIG. 12 is indicative of areas in the synthetic line images 98 that lie above or below the zero crossing plane. One or more splines 96 can be positioned across each of the synthetic line images 98. The direction of the spline(s) 96 used for the computation is preferably approximately orthogonal to the synthetic line images 98.

Figure 13:
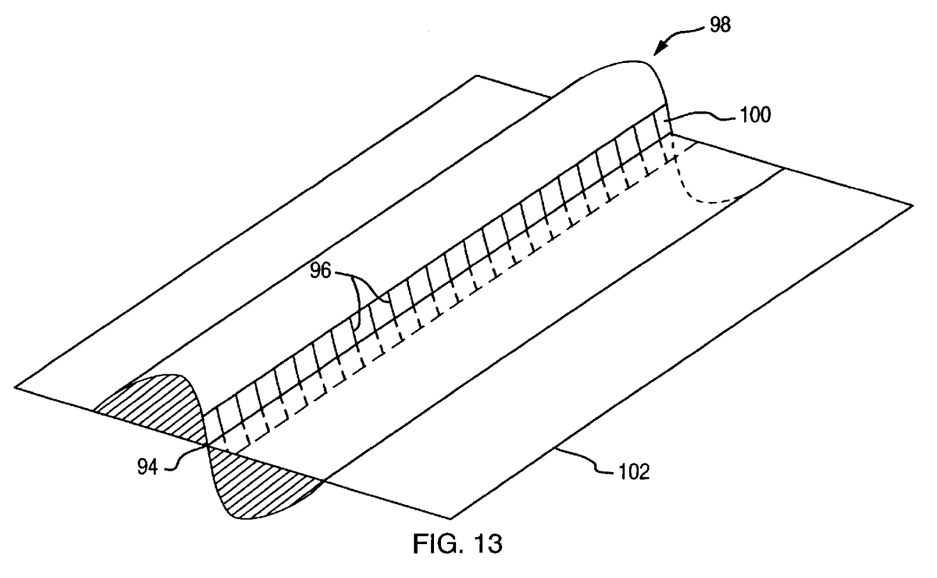
FIG. 13 is a three-dimensional diagrammatic view of a "best fit" surface fit to a synthetic line image having, according to another method of the present invention.

According to another preferred method, a "best fit" surface 100, FIG. 13, is fit to a plurality of splines 96 on each synthetic light image 98, for example, using a best fit (e.g., least square error) equation. This method then includes solving numerically for the curve that defines the intersection of the "best fit" surface 100 with the zero plane 102. The best fit surface 100 is computed for the ribbon shaped region in the vicinity of the intersection of the synthetic line image 98 with the zero crossing plane 102. This ribbon shaped region may be arbitrarily extended further above and below the zero plane 102 to encompass more pixel values into the best fit, which enhances the smoothness of the resulting fit and reduces quantizing noise. Before the pixel values are incorporated into the best fit equation, any bad pixel values can be removed, for example, via standard filtering techniques, such as use of the median filter, as is well known in the field of image processing.

Figure 14A:
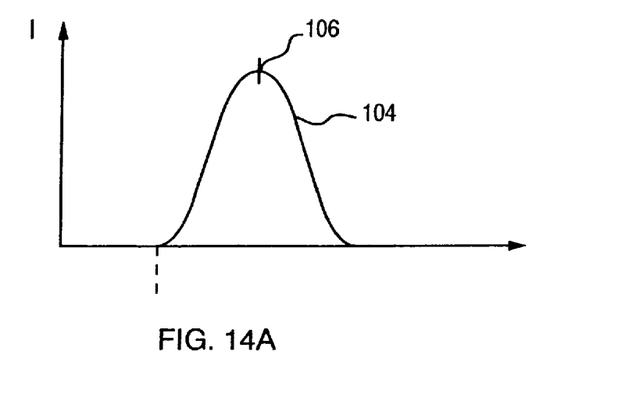
FIGS. 14A–14C are diagrammatic views illustrating the apparent "shift" of the centroid of a projected line image on surfaces having rapidly varying reflectivities.
Figure 14B:
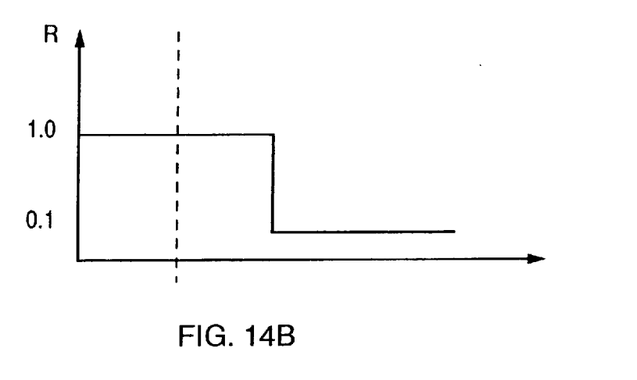
Figure 14C:
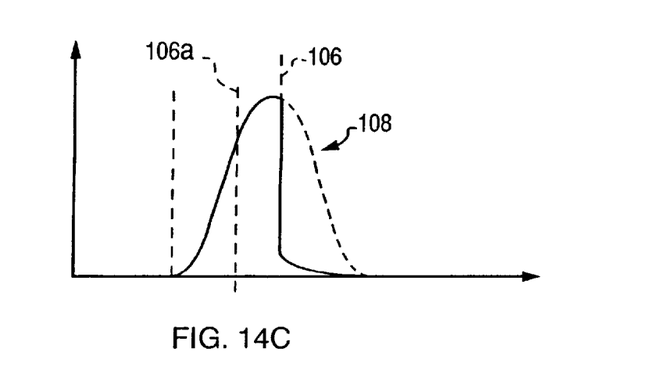
Figure 15A:
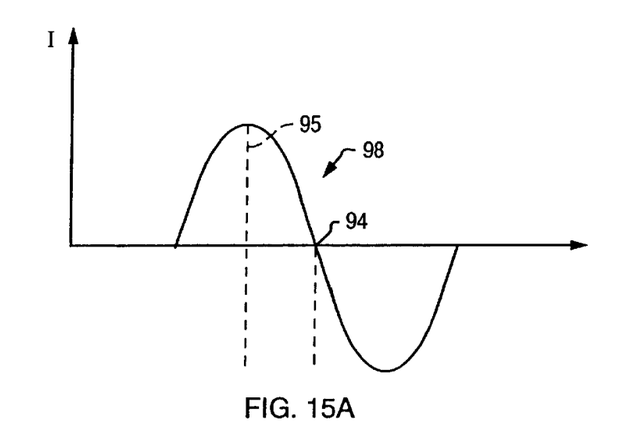
FIGS. 15A–15C are diagrammatic views illustrating the lack of a "shift" of the centroid of a synthetic line image on surfaces having rapidly varying reflectivities, according to the method of the present invention.
Figure 15B:
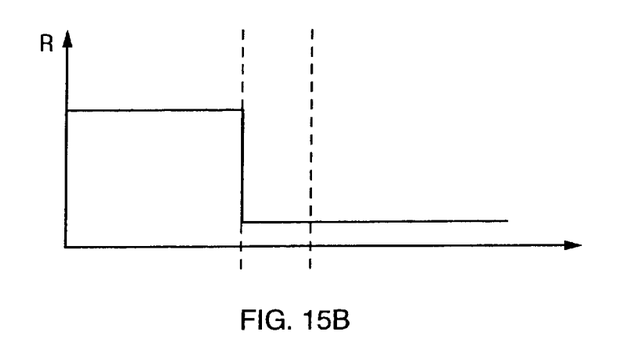
Figure 15C:
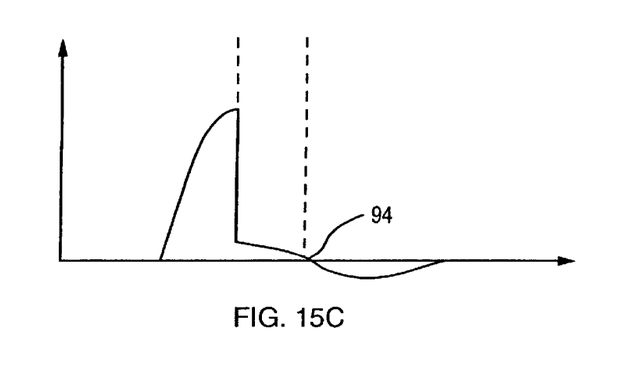

This "plane splitting" technique is particularly useful where the article being inspected has a wide range of reflectivities, such as the solder balls and substrate of a BGA device. The intensity of a projected light plane has a cross section 104, FIG. 14A, with a centroid 106. When that projected light plane impinges on an object with rapidly varying contrast, such as the change in reflectivity R shown in FIG. 14B, the centroid 106 of the light plane appears to shift in the image 108 reflected from the object, as shown in FIG. 14C. As a result of the low reflectance, the centroid 106a of the image 108 obtained by the camera appears to be to the left of the true position of the centroid 106 of the actual light plane. When the "plane splitting" technique described above is used, the zero point of the synthetic image 98, FIGS. 15A–15B, does not appear to be shifted in the image detected by the camera as a result of the difference in reflectivity. Thus, the centroid 95 of the synthetic image 98 does not appear to be shifted as a result of the change in reflectivity.

According to the preferred embodiment, the patterned light projector 20 (FIG. 2) is movable to provide the shifting of the line images 41 on the article 12. For example the patterned light projector 20 can be disposed on a 1-axis translation stage 110 that moves the projector 20 in a manner causing the line images 41 to shift. The system 10 preferably includes a projector controller 112 coupled to the translation stage, for controlling movement of the patterned light projector 20 and the shifting of the lines 41 projected onto the article 12.

Alternatively, the light patterning member 32 may include a programmable mask, such as an LCD or other similar programmable display, that enables the projected lines to be shifted electronically, thereby eliminating the need for moving parts in the system. The programmable mask can also be used to vary the line spacing depending on the spacing of the rounded specular elements 44, thereby eliminating the need for multiple slides for different types of articles 12. Where a programmable mask light patterning member 32 is used, the projector controller 112 can be coupled to the programmable mask light patterning member 32 to control the electronic shifting of the lines and the spacing of the lines on the light patterning member 32. This eliminates the need for the 1-axis translation stage 110, used to move the projector.

Figure 16A:
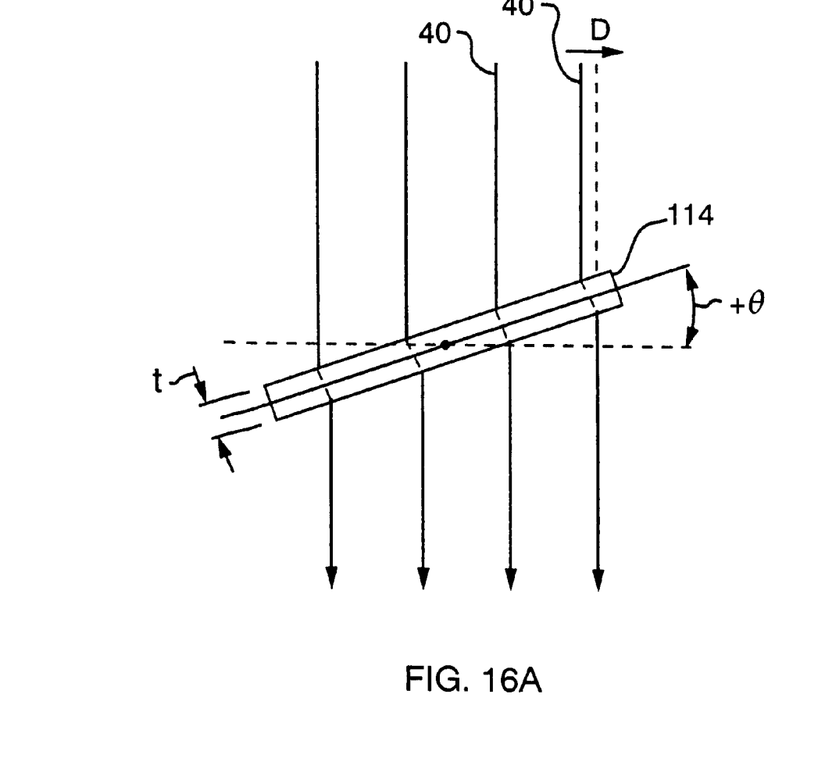
FIGS. 16A and 16B are schematic views of a transparent light shifting plate used to shift the light planes and the lines projected onto the article, according to one embodiment of the present invention.
Figure 16B:
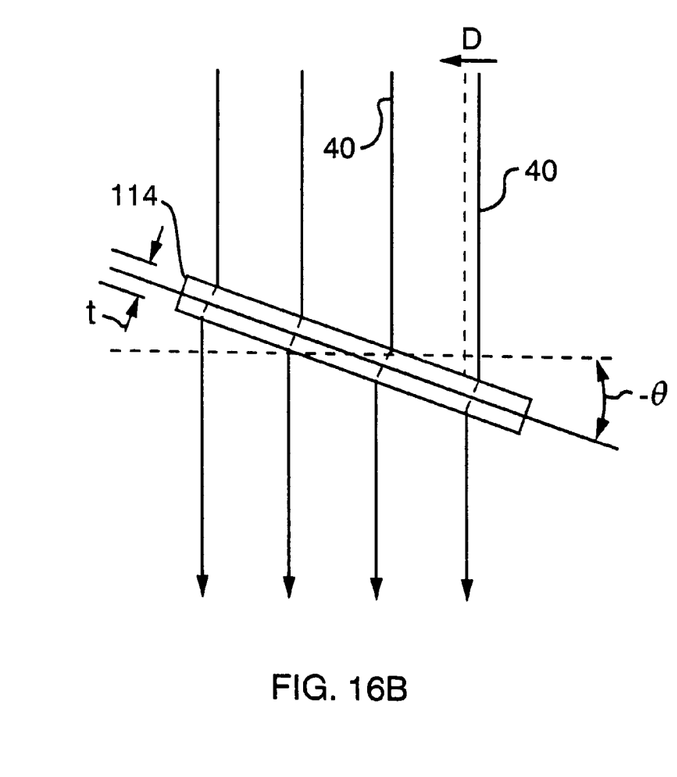

According to a further alternative, the projector 20 (FIG. 2) can include a transparent light shifting plate 114 disposed between the second projection lens 38 and the article 12. The preferred embodiment of transparent light shifting plate 114, FIGS. 16A and 16B, is made of a transparent material, such as glass or plastic, that causes the light traveling through the plate 114 to be refracted, resulting in a shift D of the projected light planes 40 and thus a shifting of the line images. The magnitude of the shift D is determined by the index of refraction of the plate 114, the thickness of the plate 114, and the angle θ at which the plate 114 has been rotated with respect to the 6 incident light. For example, the light shifting plate 114 is rotated through a first position, FIG. 16A, to an angle of +θ, causing the projected light planes 40 to shift to the right. Rotating the plate 114, FIG. 16B, in an opposite direction to a position at −θ causes the light planes 40 to shift in the opposite direction. For small angles θ, the shift D is determined according to equation (1):

$$D \cong t \cdot I\left(\frac{N-1}{N}\right) \qquad \text{Equation 1}$$

where t equals the thickness of the plate 114, I is the tangent of the angle θ, and N is the index of refraction of the material. A servomotor, mechanical cam mechanism, or other similar mechanism can be used to rotate the light shifting plate 114 between the two positions.

In one example, the three-dimensional inspection system 10 can be used with a two dimensional inspection system having a ring light 116 (FIG. 2), such as that disclosed in U.S. Pat. No. 5,943,125, U.S. Pat. No. 5,828,449 and U.S. Pat. No. 5,926,557, all assigned to the assignee of the present application and incorporated herein by reference. The two dimensional inspection system is used to determine two dimensional characteristics of solder balls on a BGA device or other elements on other types of articles, such as absence or presence, location, pitch, size and shape.

Accordingly, the three-dimensional inspection system and method of the present invention projects a light pattern in a manner that reduces unwanted reflection from specular surfaces, provides a projected pattern that is in focus, and allows high resolution measurements of the reflected light pattern to determine three-dimensional information of the article being inspected.

Modifications and substitutions by one of ordinary skill in the art are considered to be within the scope of the present invention which is not to be limited except by the claims which follow.

What is claimed is:

1. A method of inspecting three-dimensional features of an article having an array of rounded specular elements, said method comprising the steps of:

placing an article on an article support such that said article generally lies in a plane;

projecting lines of light onto said article having said array of rounded specular elements, wherein a spacing of said lines of light is greater than a spacing of said rounded specular elements such that one of said lines of light approaches a top of one of said rounded specular elements while a consecutive one of said lines is on an opposite side of a consecutive one of said rounded specular elements;

detecting at least a first image of said lines of light reflected from said article at at least a first position; and processing said at least a first image to locate at least one of said lines of light projected on said article and to measure a lateral shift of said at least one of said lines of light at a point on one of said rounded specular elements, for calculating a height of said one of said rounded specular element at said point of said lateral shift.

2. The method of claim 1 wherein said article includes a ball grid array (BGA) device having an array of solder balls disposed on a substrate, wherein said spacing of said lines is greater than a pitch of said array of solder balls.

3. The method of claim 1 further including, after the step of detecting said at least a first image at said at least a first position, the steps of:

shifting said lines of light projected onto said article by a fraction of a line width to a second position;

detecting a second image of said lines of light reflected from said article at said second position; and wherein locating said at least one of said lines of light includes the steps of:

subtracting gray scale values in said second image of said at least one of said lines from corresponding gray scale values in said first image of said at least one of said lines to obtain a synthetic image of said at least one line, wherein said synthetic image extends through a zero crossing plane and includes positive pixel values above said zero crossing plane and negative pixel values below said zero crossing plane; and locating points at which said synthetic image intersects said zero crossing plane, wherein said points at which said synthetic image Intersects said zero crossing plane are used to calculate said lateral shift of said at least one of said lines.

4. The method of claim 3 wherein said step of locating said points at which said synthetic image intersects said zero crossing plane includes fitting a plurality of best fit splines to a portion of said synthetic image proximate said zero crossing plane and determining where said best fit splines intersect said zero crossing plane.

5. The method of claim 3 wherein said step of locating said points at which said synthetic image intersects said zero crossing plane includes fitting a best fit plane to a portion of said synthetic image proximate said zero crossing plane and determining where said best fit plane intersects said zero crossing plane.

6. The method of claim 1 wherein said lines are projected onto said article such that said lines are in focus in a plane generally parallel to said plane of said article.

7. The method of claim 1 wherein projecting said lines onto said article includes providing a lower f-number in a direction along a length of said lines of light projected onto said article and a higher f-number in a direction along a width of said lines of light projected onto said article.

* * * * *